United States Patent [19]
Bryars

[11] Patent Number: 6,077,275
[45] Date of Patent: Jun. 20, 2000

[54] SPEEDBAND INTUBATION PLUG

[75] Inventor: Gayjoy M. Bryars, Marlboro, Mass.

[73] Assignee: Boston Scientific Corporation, Natick, Mass.

[21] Appl. No.: 09/057,936

[22] Filed: Apr. 9, 1998

[51] Int. Cl.[7] .................................................. A61B 17/10
[52] U.S. Cl. .......................... 606/139; 606/144; 606/190
[58] Field of Search .................................. 606/139, 144, 606/148, 190

[56] References Cited

U.S. PATENT DOCUMENTS

| | | |
|---|---|---|
| Re. 35,595 | 8/1997 | Six . |
| 3,760,810 | 9/1973 | Van Hoorn ............................... 128/326 |
| 4,418,693 | 12/1983 | LeVeen et al. ....................... 128/303 R |
| 4,794,927 | 1/1989 | Yoon ........................................ 606/140 |
| 4,876,126 | 10/1989 | Takemura et al. . |
| 4,936,835 | 6/1990 | Haaga . |
| 5,049,138 | 9/1991 | Chevalier et al. . |
| 5,080,655 | 1/1992 | Haaga ...................................... 604/265 |
| 5,141,516 | 8/1992 | Detweiler ................................. 606/154 |
| 5,158,563 | 10/1992 | Cosman .................................... 606/140 |
| 5,180,392 | 1/1993 | Skeie et al. ................................ 623/11 |
| 5,203,863 | 4/1993 | Bidoia ...................................... 606/140 |
| 5,551,946 | 9/1996 | Bullard . |
| 5,591,130 | 1/1997 | Denton . |
| 5,669,918 | 9/1997 | Balazs et al. ............................ 606/139 |
| 5,827,291 | 10/1998 | Fucci et al. .............................. 606/104 |

FOREIGN PATENT DOCUMENTS

WO97/32528  9/1997  Canada ........................... A61B 17/12

*Primary Examiner*—Michael Buiz
*Assistant Examiner*—Daphna Shai
*Attorney, Agent, or Firm*—Kenyon & Kenyon

[57] ABSTRACT

The present invention is directed to a plug for insertion into a distal end of a ligating unit including an aspiration cylinder coupled to a distal end of an endoscope. The plug comprises a mounting portion sized to fit within an opening formed in a distal end of the aspiration cylinder and a protruding portion extending away from the mounting portion to project distally from the aspiration cylinder when the insertion plug is mounted in the aspiration cylinder.

10 Claims, 3 Drawing Sheets

SPEEDBAND INTUBATION PLUG

FIELD OF THE INVENTION

The present invention relates to devices for ligating lesions within body lumens and more particularly relates to a plug for insertion into an open end of a ligating device for intubation.

BACKGROUND INFORMATION

Devices were known for ligating lesions by dispensing an elastic band from the outside of an aspiration cylinder of the device over a lesion which has been drawn into the aspiration cylinder. As these devices generally included only one ligating band, the distance between a proximal end of the aspiration cylinder which is coupled to the endoscope and the distal end was relatively small. However, if the user desired to use such a device to ligate multiple lesions, it was necessary to remove the device from the body lumen after each ligation and reload a new ligating band on the aspiration cylinder. This was time consuming and the repeated insertion of the device into the body lumen can cause discomfort to the patient.

Thus, devices have been developed which can dispense each of a plurality of ligating bands over a multiple lesions without removing the device from the body to reload. A device for conveniently dispensing ligation bands in a sequential manner is shown in U.S. Pat. No. 5,398,844 to Zaslavsky et al., the entire disclosure of which is incorporated herein by reference. Such a ligating unit may include, for example, a plurality of ligating bands disposed on an outer surface of the aspiration cylinder for release onto lesions within the body by manipulation of a pull cord coupled to the bands.

However, as the number of ligating bands received on the aspiration cylinder has increased, there has been a corresponding increase in the length of the aspiration cylinders. The increased length of the aspiration cylinder can increase discomfort to the patient as the steerability of the distal end of the endoscope is compromised.

SUMMARY OF THE INVENTION

The present invention is directed to a plug for insertion into a distal end of a ligating unit including an aspiration cylinder coupled to a distal end of an endoscope. The plug comprises a mounting portion sized to fit within an opening formed in a distal end of the aspiration cylinder and a protruding portion extending away from the mounting portion to project distally from the aspiration cylinder when the insertion plug is mounted in the aspiration cylinder.

DETAILED DESCRIPTION

Figure 1:
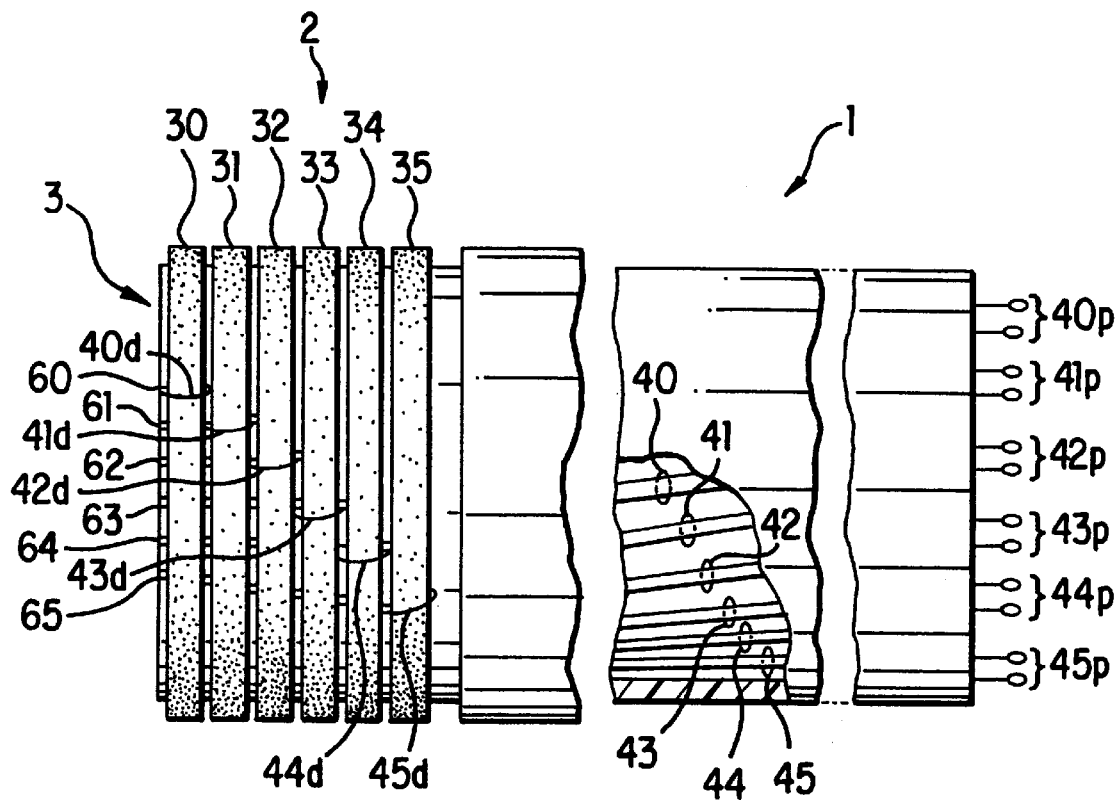
FIG. 1 shows a side view of a ligating unit as is known in the prior art.

FIG. 1 shows an aspiration cylinder 2 formed at the distal end of a known ligating unit 1, wherein a the aspiration cylinder 2 has a generally tubular shape and an open distal end 3. The ligating unit 1 may have multiple ligation bands 30–35 placed circumferentially around the aspiration cylinder 2. While on the ligating unit 1, the ligation bands 30–35 are in a stretched condition. The ligation bands 30–35 are connected to distal ends 40d–45d of filaments 40–45. Each filament 40–45 extends from its respective ligation band 30–35, through the interior of the ligating unit 1, and out the proximal end of the ligating unit 1, so that a proximal end 40p–45p of each filament 40–45 is accessible to a user.

In operation, the ligating unit 1 may be inserted into, for example, an esophagus (or other body lumen) in order to provide access into the esophagus for medical treatment and the like. For example, lesions and such may be treated by inserting the ligating unit into the esophagus so that the lesion to be treated is located at the distal end 3 of the aspiration cylinder 2. The lesion may then be drawn into the aspiration cylinder 2 by, e.g., application of suction or the use of a gripping device via the working channel of the endoscope. When the lesion has been drawn into the aspiration cylinder, the user may pull the filament 40 corresponding to the distal-most ligation band 30 in order to draw the ligation band 30 distally from the aspiration cylinder 2. The ligation band 30, when removed from the ligating unit 1, constricts around the lesion, cutting off blood supply so that the tissue is eventually sloughed off by the body. Of course, other methods of removing lesions such as the use of electrosurgical severing snares, may be employed in conjunction with the ligation bands 30–35 as is known in the art. The procedure may be similarly repeated on other lesions using, in sequence, ligation bands 31–35.

Figure 2:
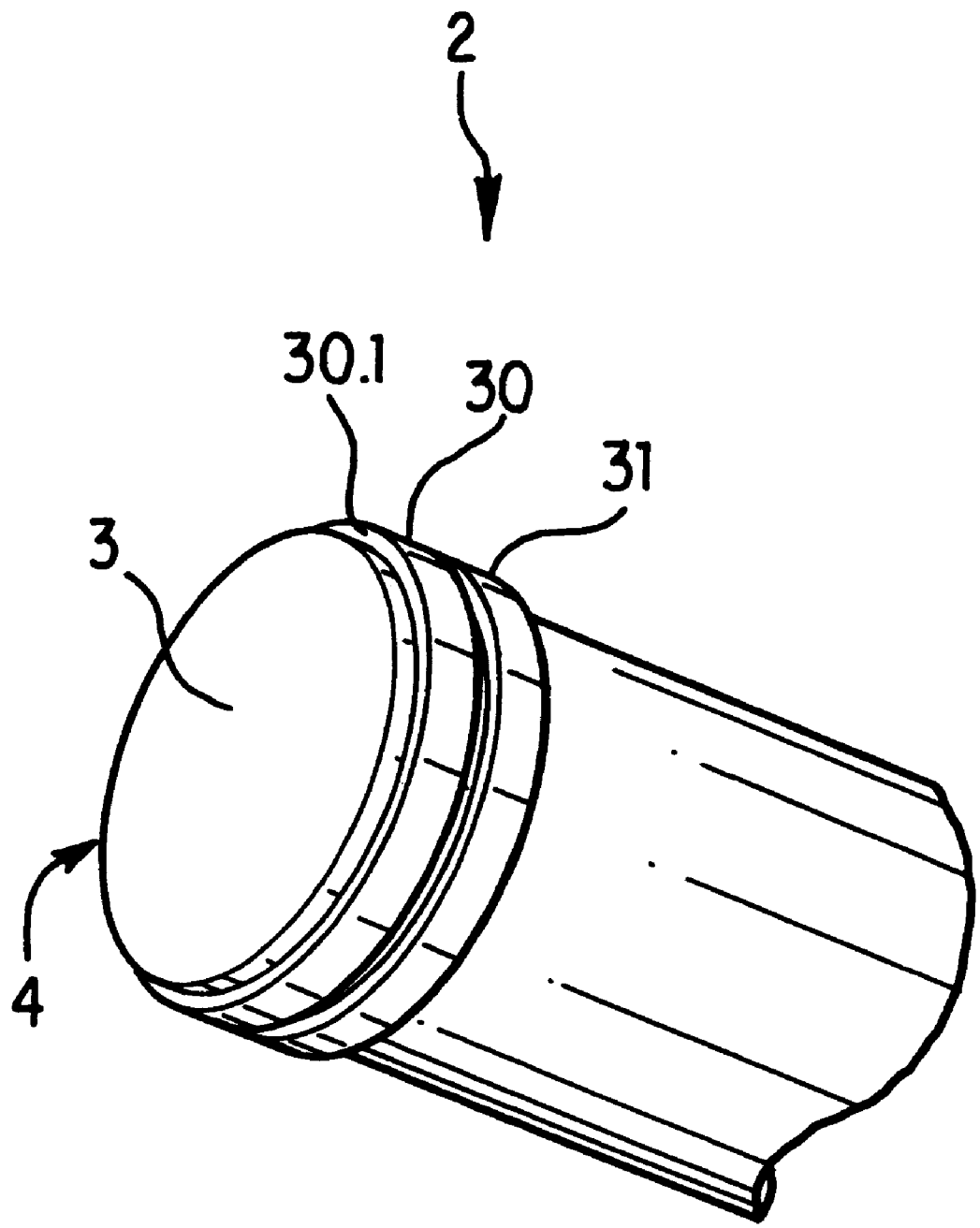
FIG. 2 shows a perspective view of the distal end of the ligating unit of FIG. 1.

However, intubation of the ligating unit 1 may be complicated by the interaction of the distal end 3 with the walls of the body lumen into which the ligating unit 1 is being inserted as the aspiration cylinder extends well beyond the distal end of the endoscope. For example as shown in FIG. 2, the distal end 3 has an exposed edge 4 that may catch on the walls of the esophagus as the ligating unit 1 is being inserted into the esophagus. Also, the distal ligation band 30 forms an edge 30.1 with the ligating unit 1. The edge 30.1 may interact with the wall of the cavity into which the ligating unit 1 is being inserted. To reduce the interaction of the edge 4 of the distal end 3 and of the edge 30.1 of ligation band 30 with the walls of the cavity, an insertion plug 10 may be inserted into the distal end 3 of the ligating unit 1. In addition, as the surface area of the ligating bands exposed on the outer surface of the aspiration cylinder 2 increases, resistance to the passage of the ligating unit 1 through the body lumen will also be increased. As this may cause irritation to the lining of the body lumen, it is desired to reduce the amount and severity of contact between the outer surface of the aspiration cylinder 2 and the lining of the body lumen.

Figure 3:
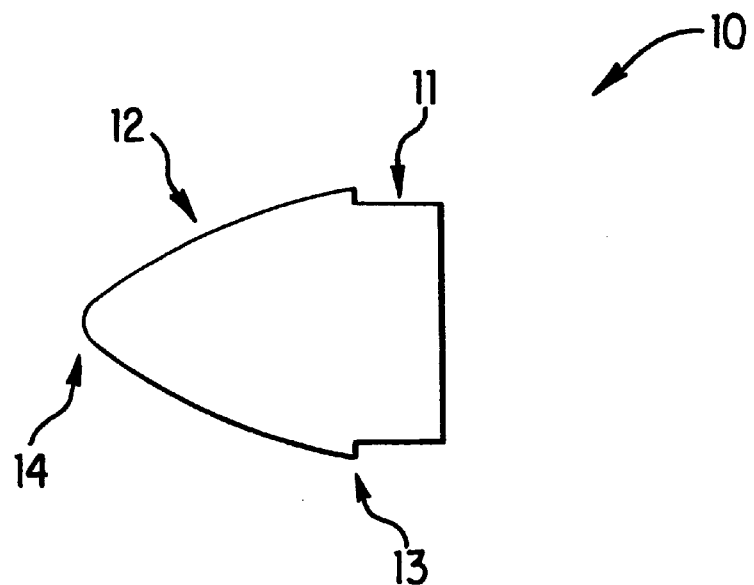
FIG. 3 shows a side view of an insertion plug according to the present invention.
Figure 4:
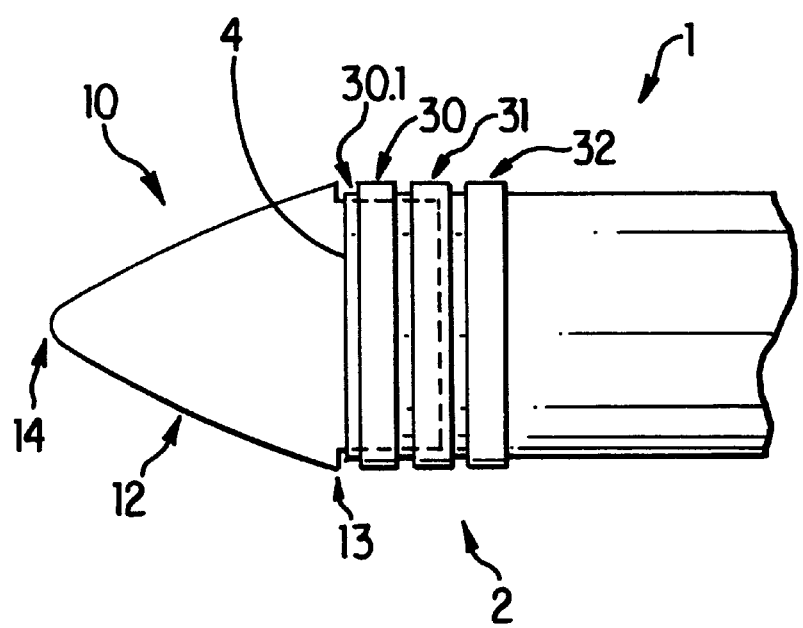
FIG. 4 shows a side view of a ligating unit with an insertion plug inserted therein.

FIG. 3 shows an insertion plug 10 according to the present invention, which includes a proximal mounting end 11 adapted to fit snugly into the aspiration cylinder 2 of the ligating unit 1 and a distal protruding end 12 which remains outside of the ligating unit 1. The protruding end 12 of the plug 10 may be flat or, may more preferably be formed with a curved or rounded shape to avoid the formation of any edges which may irritate the body lumen or impede insertion of the device 1. The insertion plug 10 may also be profiled to provide, for example, a lip 13 between the mounting end 11 and an increased diameter portion which remains outside the aspiration cylinder 2 when the plug 10 is mounted thereon. The lip 13 being sized to radially cover the edge 30.1 of the distal ligation band 30, and thereby reduce interaction of edge 30.1 with the wall of the esophagus during intubation. In addition, this lip 13 may provide a shoulder against which the distal end 3 of the aspiration cylinder 2 may be pressed to ensure proper installation. Thus the insertion plug 10, when mounted on the aspiration cylinder 2, preferably covers the edge 4 of the ligating unit 1 and the edge 30.1 of the distal ligation band 30 to make intubation of the ligating unit 1 easier. To further ease intubation, the insertion plug 10 may have a tapered shape on the distal end. For example, the insertion plug 10 may have a relatively conical shape in which the diameter of the second end 12 is greatest adjacent to the lip 13 and gradually tapers down to a relatively blunt distal tip 14. Of course, those skilled in the art will recognize that, even if the outer diameter of the proximal portion of the plug 10 is selected to be only equal to (or slightly greater than) that of the aspiration cylinder 2, problems associated with contact between the edge 4 and body tissues will be reduced. By covering the exposed edge 4 and the extension of the ligation bands 30–35 away from the surface of the aspiration cylinder 2, irritating contact and snags between these edges and body tissues is further reduced. Then, when the device 1 has been inserted to a desired location within the body lumen, the plug 10 my be flushed out of the aspiration cylinder 2 by, for example, applying fluid through a working channel of the endoscope.

According to one embodiment of the invention, the insertion plug 10 is made of a material that can absorb radiographic contrast liquids so that the insertion plug 10 may become opaque to X-rays. Thus, a surgeon may be able to detect a precise location of the insertion plug 10 during a medical procedure.

Appropriate materials from which the insertion plug 10 may be made include, for example, water soluble polymers such as polyvinyl alcohol, polyethylene oxide, polyethylene glycol, polyacrylamides, polyvinyl pyrolidone, polyacrylic acid, and the like.

While the present invention is capable of various modifications and alternate constructions, it is not intended to limit the invention to the specific embodiments disclosed herein. Rather, it is intended to cover all modifications and alternative constructions falling within the spirit and scope of the invention as expressed in the claims.

What is claimed is:

1. A ligation unit, comprising:

an aspiration cylinder having a generally tubular shape and defining an opening in a distal end thereof;

a ligation band placed circumferentially around the aspiration cylinder;

a filament, the filament connected at a distal end to the ligation band, the filament extending from the ligation band through an interior of the aspiration cylinder wherein a proximal end of the filament extends out of a proximal end of the aspiration cylinder; and a plug, the plug including:

a mounting portion sized to fit within the opening in the distal end of the aspiration cylinder; and a protruding portion extending away from the mounting portion to project distally from the distal end of the aspiration cylinder when the insertion plug is mounted in the aspiration cylinder.

2. The ligation unit according to claim 1 wherein the plug is made of a water soluble material.

3. The ligation unit according to claim 1 wherein the protruding portion is tapered from a maximal outer diameter at an abutting portion which, when the plug is mounted in the aspiration cylinder, is located adjacent to the distal end of the aspiration cylinder to a reduced diameter rounded end which, when the plug is mounted in the aspiration cylinder, is located furthest distally from the aspiration cylinder.

4. The ligation unit according to claim 3, wherein the abutting portion forms a lip extending radially outwardly from the mounting portion so that, when the mounting portion is received within the opening in the distal end of the aspiration cylinder, the lip abuts the distal end of the aspiration cylinder.

5. The ligation unit according to claim 4, wherein the lip is adapted to cover a distal edge of the ligation band.

6. The ligation unit according to claim 1, wherein the plug is made of a material that absorbs radiographic contrast fluids.

7. The ligation unit according to claim 1, wherein the plug is formed of a water soluble polymer.

8. The ligation unit according to claim 7, wherein the material from which the plug is made is selected from the group consisting of polyvinyl alcohol, polyethylene oxide, polyethylene glycol, polyacrylamides, polyvinyl pyrolidone and polyacrylic acid.

9. The ligation unit according to claim 1 wherein the mounting portion is releasably frictionally secured to a longitudinal portion of the aspiration cylinder.

10. The ligation unit according to claim 9 wherein the mounting portion is frictionally secured to an inner surface of the longitudinal portion of the aspiration cylinder.

\* \* \* \* \*